United States Patent [19]

Imai et al.

[11] Patent Number: 5,693,480

[45] Date of Patent: Dec. 2, 1997

[54] METHOD AND REAGENT FOR DETERMINNG EXO-TYPE SACCHARIDE HYDROLASE ACTIVITY

[75] Inventors: Yasuhiko Imai, Nagareyama; Shoichi Tokutake, Noda; Masaru Suzuki, Nagareyama; Nobuyuki Yamaji, Noda, all of Japan

[73] Assignee: Kikkoman Corporation, Noda, Japan

[21] Appl. No.: 501,870

[22] Filed: Jul. 13, 1995

[30] Foreign Application Priority Data

Jul. 18, 1994 [JP] Japan .................. 6-165608

[51] Int. Cl.$^6$ .................. C12Q 1/34; C07G 3/00
[52] U.S. Cl. .................. 435/18; 536/4.1
[58] Field of Search .................. 536/4.1

[56] References Cited

FOREIGN PATENT DOCUMENTS 6-46895  2/1994  Japan .

OTHER PUBLICATIONS

Agric. Biol. Chem. 47 (8), 1741–1746 Seiya et al. (1983).

*Primary Examiner*—Johann Richter
*Assistant Examiner*—Ebenezer Sackey
*Attorney, Agent, or Firm*—Banner & Witcoff, Ltd.

[57] ABSTRACT

According to this invention are provided a method for determining an exo-type saccharide hydrolase activity which comprises adding to a sample a β-maltoside derivative represented by the general formula

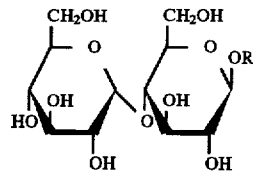

wherein R is a chromophoric organic group, as a substrate, conducting reaction in the presence of a coupled enzyme, and optically determining the substance liberated, and a method for differentially determining glucoamylase and α-glucosidase activities which comprises adding, to a sample, the above β-maltoside derivative as the first substrate and a coupled enzyme, and an α-glucoside derivative represented by the general formula

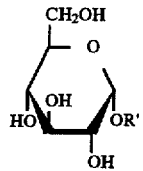

wherein R' is a chromophoric organic group, as the second substrate, subjecting the mixtures to separate enzymatic reactions, and then optically quantitatively determine the substances liberated.

8 Claims, 10 Drawing Sheets

METHOD AND REAGENT FOR DETERMININNG EXO-TYPE SACCHARIDE HYDROLASE ACTIVITY

BACKGROUND OF THE INVENTION (1) Field of the Invention

This invention relates to a method for determining an exo-type saccharide hydrolase activity. More specifically, this invention relates to a method for rapidly and accurately determining the activity of an enzyme, among exo-type saccharide hydrolases, which hydrolyzes the α-1,4-glucoside chain from the non-reducing end using a β-maltoside derivative as a substrate, and a reagent therefor, and, when a mixture of glucoamylase and α-glucosidase, which are exo-type saccharide hydrolases, is used as an enzyme sample, a method for differentially determining the activities of these enzymes by determining the enzymatic activities using a β-maltoside derivative and an α-glucoside derivative as substrates, respectively.

Therefore, this invention plays a very important role not only in the brewing field, but widely in the fields of a food industry, starch industry, clinical diagnoses, etc.

(2) Description of the Related Art

Among exo-type saccharide hydrolases, glucoamylase and α-glucosidase, which are enzymes hydrolizing the α-1,4-glucoside chain from the non-reducing end to form glucose, play an important role in the brewing, food, starch industries, etc.

In the determination of glucoamylase activity, a method which comprises determining the amount of glucose formed using a soluble starch as a substrate, and thereby looking for its active value ["Annotation of No. 4 Revised Assays Prescribed by National Tax Administration Agency" edited by Annotation Editing Committee, page 213, Japan Brewing Association (1993)] is so far general. However, this method has defects, for example that (1) in the case of a sample containing much glucose such as an extract of Koji, it is difficult to subject the sample directly to the determination, and it is necessary to previously dialyze the sample, (2) operations therefor are complicated and it takes a long time for the assay, because the assay is conducted by two steps of the reaction of making the sample act on a substrate to form glucose and the reaction of quantitatively determining the formed glucose, and (3) when α-amylase is also present in the sample, the value to be measured is influenced thereby.

On the other hand, there are known a method which comprises conducting the decomposition of a soluble starch and the determination of glucose formed in the same reaction solution ["Seibutsu Kogakukai-shi"], volume 71, page 93 (1993)], and a method which comprises using phenyl α-glucoside or 2,4-dinitrophenyl-α-glucoside as a substrate for determining glucoamylase (Japanese Patent Kokai No. 51-85790). However, although the former method has an advantage of being simple and not influenced by α-amylase, it has a defect that the assay becomes difficult when glucose is contained in the sample, and on the other hand, although the latter method has an advantage of being not influenced by glucose in the sample and being conducted by simple assay operations, it is not practical because the reactivity of glucoamylase on this substrate is poor.

Further, although both enzymes of glucoamylase and α-glucosidase are contained, for example in rice Koji as exo-type saccharide hydrolases, an attempt to differentially determine these enzymes has not so far been made.

SUMMARY OF THE INVENTION

The object of this invention is to provide a novel method for determining an exo-type saccharide hydrolase activity which has overcome defects which such usual methods for determining an exo-type saccharide hydrolase activity have, is such a method that there is not need to conduct dialyzation if glucose is contained in the sample, is not influenced if α-amylase is also present in the sample, and makes it possible to determine the exo-type saccharide hydrolase activity in the sample rapidly and with high sensitivity, and a reagent for the determination to be used therefor, and further provide, when glucoamylase and α-glucosidase are contained in the sample, a method for differentially determining them with good efficiency.

The present inventors had made sequential researches for attaining the above objects, and as a result, they found that when among β-maltooligoside derivatives, one wherein two glucoses are bound is used as a substrate, the two exo-type saccharide hydrolases selectively hydrolyze the α-1,4-glucoside chain of the β-maltooligoside derivative from the non-reducing end, and moreover, their reactivities are very high, but α-amylase does not act thereon. Thus, the present inventors found that a β-maltoside derivative wherein two glucoses are bound is an optimum substrate for determination of the activity of the two exo-type saccharide hydrolases, and further found that when glucoamylase and α-glucosidase are contained in the sample, the respective activities can be differentially determined with good efficiency, by using the above β-maltoside derivative as the first substrate and using a specific α-glucoside derivative as the second substrate, and completed this invention based on these findings.

Thus, this invention provides a method for determining an exo-type saccharide hydrolase activity which comprises subjecting a sample containing the exo-type saccharide hydrolase to enzymatic reaction, using a β-maltoside derivative represented by the general formula:

(I)

wherein R is a chromophoric organic group, as a substrate, and β-glucosidase, and then quantitatively determine the chromophoric substance liberated.

Further, this invention also provides a method for differentially determining glucoamylase and α-glucosidase activities which comprises subjecting a sample containing at least one of glucoamylase and α-glucosidase to enzymatic reactions, using, as the first substrate, a β-maltoside derivative represented by the general formula:

(I)

wherein R is a chromophoric organic group, in the presence of β-glucosidase, and using, as the second substrate, an α-glucoside derivative represented by the general formula:

(II)

wherein R' is a chromophoric organic group, and having such a property that the reaction rate ratio between glucoamylase and α-glucosidase is different from that on the first substrate, and then quantitatively determining the chromophoric substances liberated.

Herein, the chromophoric organic group means a group capable of becoming an optically detectable chromophoric organic compound and leaving, when the enzymes are made to act on the substrate.

DESCRIPTION OF THE PREFERRED EMBODIMENT

This invention is detailedly described below.

As a system advantageous for determining an exo-type saccharide hydrolase activity, there can, for example, be mentioned a system of pH 3 to 10 which contains 0.2 to 20 mM of a β-maltoside derivative represented by the above general formula (I) and 2 to 300 mM of a buffer, and further contains 0.5 to 30 units/ml of β-glucosidase as a coupled enzyme.

As the above β-glucosidase, one derived from any origin such as a microorganism or a plant may be used, and for example, one obtained from a seed of an almond is used.

Next, among the methods of this invention, an embodiment suitable for determining an exo-type saccharide hydrolase activity is described. First, to a sample containing an exo-type saccharide hydrolase is added 0.5 to 30 units/ml, preferably 1 to 15 units/ml of β-glucosidase as a coupled enzyme, at the same time or thereafter, 0.2 to 20 mM, preferably 0.5 to 10 mM of a β-maltoside derivative represented by the general formula (I) is added together with a buffer, the mixture is subjected to enzymatic reaction under conditions of a temperature of 25° C. to 45° C., preferably 35° C. to 40° C. and a pH of 3 to 10, preferably 4 to 7, for at least 1 minute, preferably 2 to 10 minutes, the amount of the chromophoric substance formed is determined in a usual way by measuring, directly or after a further condensation reaction or after the adjustment of pH, the variation of absorbance continuously or intermittently at an appropriate wavelength, and the enzymatic activity is calculated from the molecular extinction coefficient of the used chromophoric substance.

As buffers usable for this system, there can, for example, be mentioned phosphates, acetates, carbonates, Good's buffers, borates, citrates, β-glycerophoshates, dimethylglutarates, etc.

Besides the above components, various conventional additives such as solubilizers and stabilizers, e.g., glycerol, bovine serum albumin, α- or β-cyclodextrin, Triton X-100, etc. can, if necessary, be added to such systems, within a range not to spoil the object of this invention. These additives may be used alone or in combination of two or more. These additives may be added at the stage of the preparation of the above system.

As to the sample containing the exo-type saccharide hydrolase used in this invention, any sample may be used so long as it exhibits an exo-type saccharide hydrolase activity, and there is no particular limitation thereon, but specifically, there may be used extracts of solid cultures of microorganisms and liquid culture broths of microorganisms, extracts of plants, or humors and tissues of animals and extracts thereof, etc. When such a sample is solid, it is convenient to once dissolve or suspend it in purified water or a buffer as mentioned above. Further, if necessary, it is possible to remove the insoluble matter by filtration or the like.

When a sample containing both enzymes of glucoamylase and α-glucosidase, for example an extract of rice Koji, soybean Koji or the like is used, in the determination of this invention where the β-maltoside derivative alone is used as the substrate, the sum of the activity values of both enzymes of glucoamylase and α-glucosidase is obtained as determinations. In such a case, it is possible to assume the determination result itself as the saccharification power (glucose forming activity) of the Koji. The reason is that even in the determination method of the usual glucoamylase activity using a soluble starch as a substrate, when α-glucosidase is also present therein, the α-glucosidase activity is contained in the determinants (The Abstracts of the 1993 Mass Meting of Japan Brewing Society, page 7), and the saccharification power (glucose forming activity) of the Koji becomes an important index in brewing steps. Further, when the activities of glucoamylase and α-glucosidase among the exo-type saccharide hydrolases are to be differentially determined, the respective activities can be determined according to the differential determination method of this invention using the β-maltoside derivative and the α-glucoside derivative.

The method of differentially determining the activities of both enzymes of glucoamylase and α-glucosidase among exo-type saccharide hydrolases is specifically described below. First, the reaction rate on the first substrate is previously determined according to the aforementioned method, using glucoamylase and α-glucosidase whose activities are known. The reaction rate on the second substrate is then determined as follows.

Namely, 0.2 to 30 mM, preferably 5 to 20 mM of an α-glucoside derivative represented by the formula (II) is added together with a buffer to an enzyme sample, the mixture is subjected to enzymatic reaction under conditions of a temperature of 25° to 45° C., preferably 35° C. to 40° C. and a pH of 3 to 10, preferably 4 to 7, for at least 1 minute, preferably 10 to 20 minutes, the amount of the chromophoric substance formed is determined in a usual way by measuring, directly or after a further condensation reaction or after the adjustment of pH, the variable absorbance continuously or intermittently at an appropriate wavelength, and the enzymatic activity is calculated from the molecular extinction coefficient of the used chromophoric substance.

When the reaction rate constant of glucoamylase on the first substrate is expressed as $k_1$, reaction rate constant of α-glucosidase thereon as $k_2$, the variable absorbance thereon as $A_1$, the reaction rate constant of glucoamylase on the second substrate as $k_3$, the reaction rate constant of α-glucosidase thereon as $k_4$, the variable absorbance thereon as $A_2$, the glucoamylase activity in the sample as GLA, and the α-glucosidase activity therein as GLS, the following relations are present among them.

$$A_1 = k_1 \cdot GLA + k_2 \cdot GLS \quad \text{(Equation 1)}$$

$$A_2 = k_3 \cdot GLA + k_4 \cdot GLS \quad \text{(Equation 2)}$$

The following equation is derived from these equations.

$$GLA = \frac{K_4 \cdot A_1 - K_2 \cdot A_2}{K_1 \cdot K_4 - K_2 \cdot K_3} \quad \text{(Equation 3)}$$

$$GLS = \frac{K_3 \cdot A_1 - K_2 \cdot A_2}{K_2 \cdot K_3 - K_1 \cdot K_4} \quad \text{(Equation 4)}$$

Namely, when $k_1$, $k_2$, $k_3$ and $k_4$ are previously measured, the glucoamylase activity and the α-glucosidase activity in a sample can be differentially determined by only entering the absorbance variations measured by conducting the enzymatic reactions using the two substrates, in Equations 3 and 4.

As to the aromatic chromophoric groups of R and R' to be introduced into the 1-position of the reducing end glucose as a glycoside, in the β-maltoside derivative and the α-glucoside derivative represented by the general formulae (I) and (II), any aromatic chromophoric group may be used so long as it can be spectroscopically detected, but the following ones are exemplified.

wherein $R^1$ to $R^5$, which are same or different, are hydrogen atom, halogen atom, nitro group, amino group, alkyl group, aryl group, allyl group, sulfon group or carboxyl group, or $R^1$ and $R^2$, or $R^3$ and $R^4$ may bond to form a condensed aromatic ring.

wherein $R^6$ is a hydrogen atom or an alkyl group.

wherein $R^7$ is a hydrogen atom or a halogen atom.

wherein $R^8$ to $R^{15}$, which are same or different, are hydrogen atom, halogen atom, nitro group, amino group, alkyl group, aryl group, allyl group, sulfon group or carboxyl group, or $R^8$ and $R^9$, or $R^{10}$ and $R^{11}$ may bond to form a condensed aromatic ring, and further $R^9$ and $R^{10}$ and/or $R^{13}$ and $R^{14}$ may become common oxygen atom(s) and thereby form a condensed ether ring, and Z is a nitrogen atom or N→O.

Thus, as compounds represented by the general formula (I), there can, for example, be mentioned 2-chloro-4-nitrophenyl=β-maltoside, 4-nitrophenyl=β-maltoside, 2-fluoro-4-nitrophenyl=β-maltoside, phenolindo-3'-chlorophenyl=β-maltoside, resazulinyl=β-maltoside, 4-aminophenyl=β-maltoside, 4-methyl-umbelliferonyl =β-maltoside, luciferinyl=β-maltoside, etc., and as compounds represented by the general formula (I), there can, for example, be mentioned 4-nitrophenyl=α-D-glucoside, 2-chloro-4-nitrophenyl =α-D-glucoside, 4-aminophenyl =α-D-glucoside, 4-methylumbelliferonyl=α-D-glucoside, phenolindophenyl=α-D-glucoside, etc.

Any process can be used for producing the β-maltoside derivative and the α-glucoside derivative represented by the general formula (I) and (II) of this invention, but, for example, they can be produced by the glycosylation reaction of a phenol using silver oxide (Japanese Patent Kokai No. 62-283989) or by the process described in "Chem. Ber.", vol. 66, page 478 (1933).

In this invention, as the β-maltoside derivative represented by the general formula (I), it is preferred to use one represented by the general formula (III)

wherein $X^1$ and $X^2$, which are same or different are hydrogen atom, halogen atom, nitro group, amino group, alkyl group, sulfon group or carboxyl group, because its solubility in water is large, and particularly one represented by the general formula (IV)

wherein X¹ has the same meaning as mentioned above, because a large molecular extinction coefficient can be obtained.

Further, as the α-glucoside derivative represented by the general formula (II), it is preferred to use one represented by the general formula (V)

wherein X³ and X⁴ which are same or different, are hydrogen atom, halogen atom, nitro group, amino group, alkyl group, sulfon group or carboxyl group, because its solubility in water is large, as is the above case, and particularly one represented by the general formula (VI)

wherein X³ has the same meaning as mentioned above, because a large molecular extinction coefficient can be obtained.

The β-maltoside derivative used in this invention has characteristics that the rate of its hydrolysis is fast, and the number of a site to be cleaved with an exo-type saccharide hydrolase is only one, and is extremely important as a substrate for determining an exo-type saccharide hydrolase activity, and by using this derivative, it is possible to determine an exo-type saccharide hydrolase activity easily, accurately in a short time, without the influence of glucose and α-amylase contained in the sample, according to a method for automatic analysis, manual assay, etc.

Further, when both enzymes of glucoamylase and α-glucosidase are contained in the sample, both enzymatic activities can be differentially determined with good efficiency, by using the above-mentioned β-maltoside derivative, and an α-glucoside derivative having such a property that the ratio between the reaction rates of glucoamylase and α-glucosidase thereon is different from that on the β-maltoside derivative.

This invention is further detailedly described below according to examples, but this invention is not limited at all by these examples.

EXAMPLE 1

Preparation of reagents for determining an exo-type saccharide hydrolase activity (1) Preparation of a solution of a β-maltoside derivative
2-chloro-4-nitrophenyl O-α-D-glucopyranosyl-(1→4)-α-D-glucopyranoside (hereafter, abbreviated as G2-N) was dissolved in 100 mM acetate buffer (pH=4.0) so that its concentration could become 10 mM.

(2) Preparation of a solution of a coupler enzyme
β-glucosidase derived from an almond was mixed with 100 mM acetate buffer (pH=4.0) so that its concentration could become 14 U/ml and dissolved therein. As the β-glucosidase was used one commercially available from TOYOBO CO., LTD.

EXAMPLE 2

Determination of glucoamylase activity (1) Preparation of solution of a β-maltoside derivative
G2-N was dissolved in 100 mM acetate buffer (pH=4.0) so that its concentration could become 10 mM.

(2) Preparation of a solution of a coupled enzyme
β-glucosidase derived from an almond was mixed with 100 mM acetate buffer (pH=4.0) so that its concentration could become 14 U/ml and dissolved therein. As the β-glucosidase was used one commercially available from TOYOBO CO., LTD.

(3) Preparation of a glucoamylase preparation solution
Purified glucoamylase obtained from a liquid culture broth of *Aspergillus oryzae* using ion exchange chromatography and gel filtration was used after being appropriately diluted with 100 mM acetate buffer (pH=5.0). As to the activity of glucoamylase, an enzyme amount whereby 1 mg of glucose is liberated at 40° C. for 60 minutes was defined as 1 U. The assay was conducted according to "Annotation of No. 4 Revised Assays Prescribed by National Tax Administration Agency" edited by Annotation Editing Committee, page 213, Japan Brewing Association (1993).

(4) Reaction procedures
500 μl of the substrate solution and 500 μl of the coupled enzyme solution were mixed, and preliminarily incubated at 37° C. for 5 minutes. 50 μl of the glucoamylase preparation solution was added to start reaction. After the reaction at 37° C. for accurately 10 minutes, 500 μl of 0.2M $Na_2CO_3$ solution was added to stop the reaction. The absorbance of this solution at 400 nm was measured. As to blank, the mixed solution of the substrate and the coupled enzyme was incubated at 37° C. for 10 minutes, 500 μl of 0.2M $Na_2CO_3$ solution was added and mixed, and then the glucoamylase preparation solution was added. Thereafter, absorbance was measured in the same manner as above.

(5) Calculation of activity
The activity of the enzyme sample on this substrate was calculated as follows from the obtained absorbance.

$$U/ml = \frac{\Delta A \times Vt \times df}{\epsilon \times Vs \times t}$$

$$= \Delta A \times 0.1791 \times df$$

wherein U is an enzyme amount whereby 1 μmol of 2-chloro-4-nitrophenol is liberated at 37° C. for 1 minute, ΔA is a value obtained by subtracting the absorbance of blank from the absorbance of the enzyme sample, Vt is the amount of the reaction solution, df is the dilution rate of the sample, ε is the molecular extinction coefficient of 2-chloro-4-nitrophenol (17.3 $cm^2/\mu mol$), Vs is the liquid amount of the enzyme sample, and t is reaction time (minute).

Figure 1:
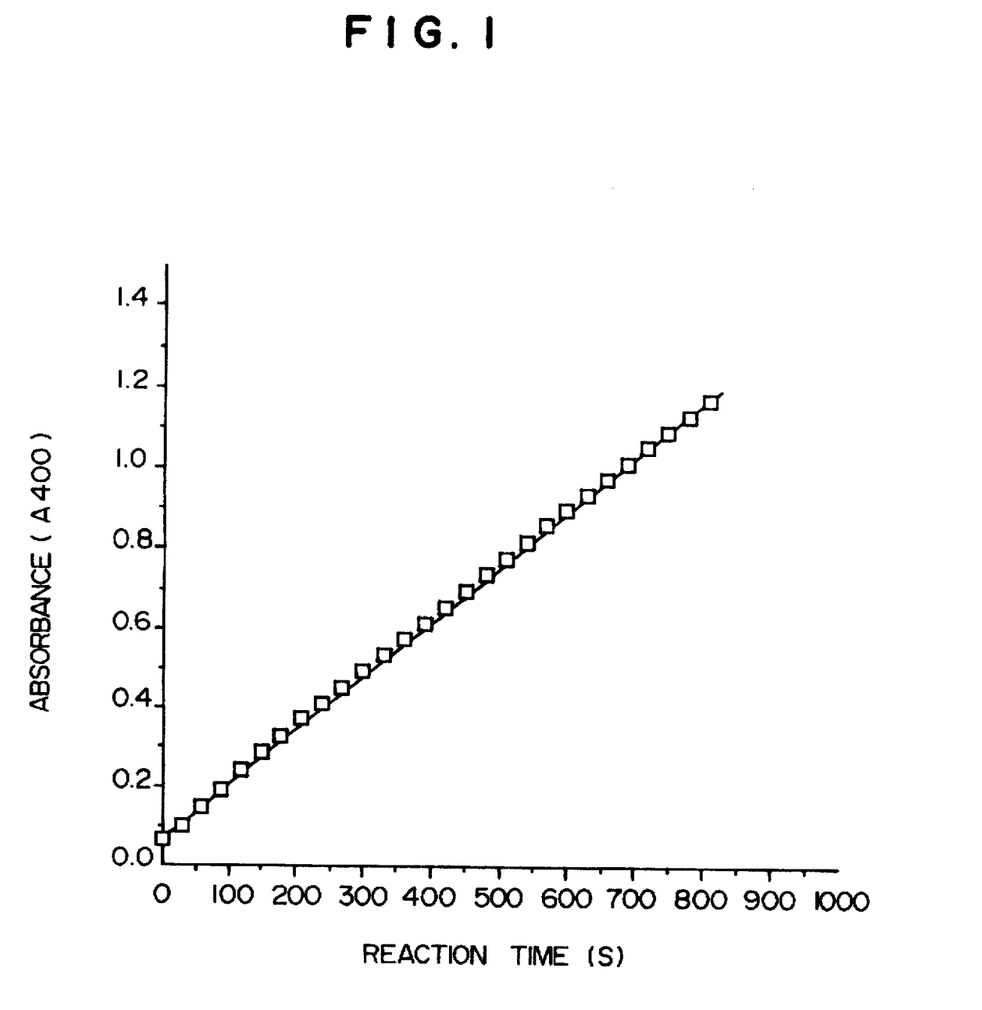
FIG. 1 is a graph showing the time course of the reaction in Example 1.

(6) Time course of reaction
Reaction was conducted using the glucoamylase preparation, and absorbance was measured. The results are shown in FIG. 1. It is seen from this drawing that linearity is maintained for at least 15 minutes.

Figure 2:
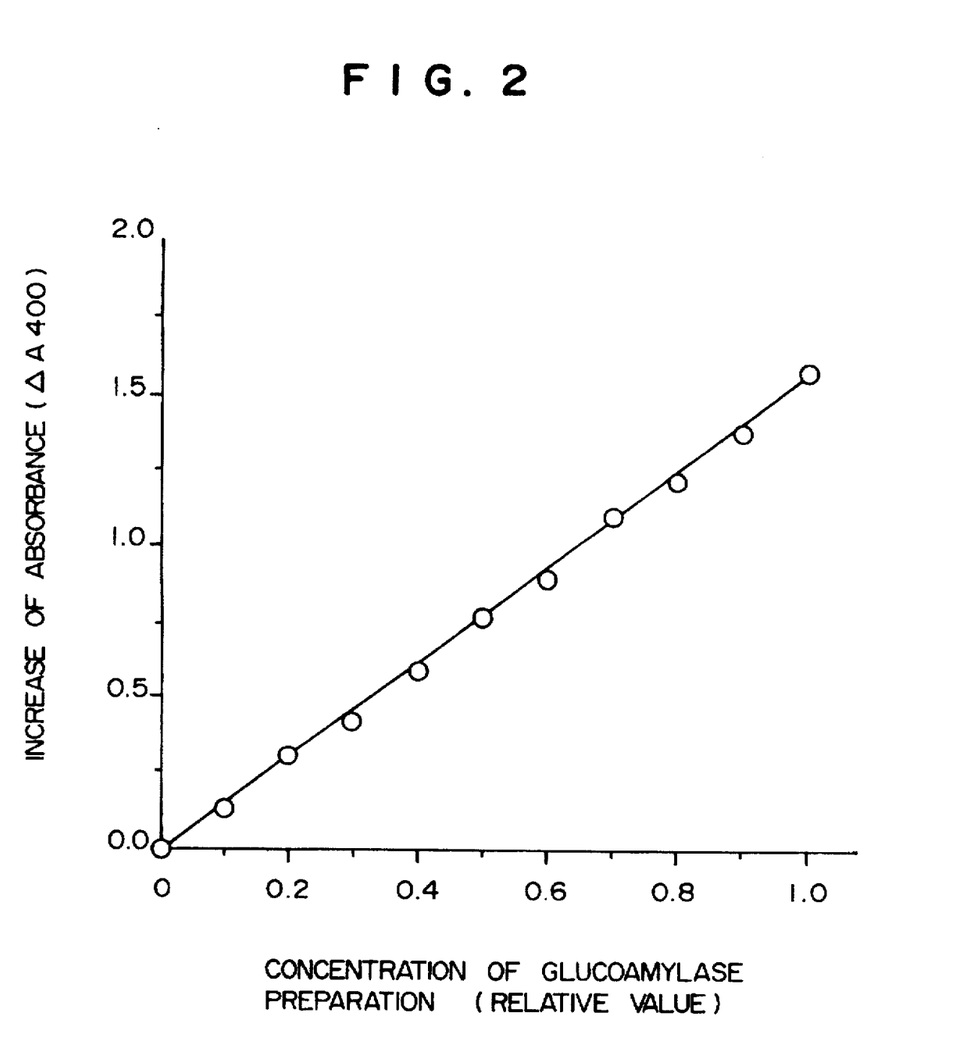
FIG. 2 is a graph showing the linearity of the reaction in Example 1.

(7) Linearity of reaction
Reaction was conducted using the glucoamylase preparation, and the increase of absorbance (ΔOD) was measured. The results are shown in FIG. 2. It is seen from this drawing that there is good linearity between the concentration of the glucoamylase and the increase of absorbance.

(8) Determination of glucoamylase activity

Figure 3:
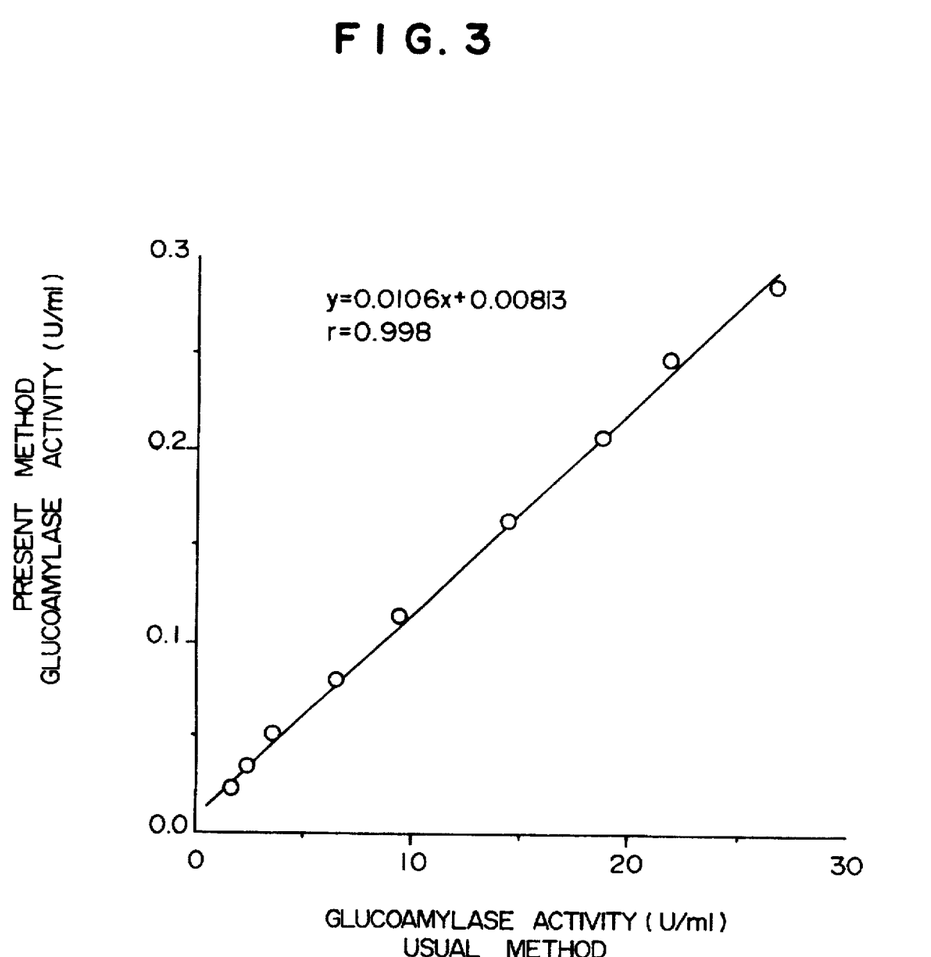
FIG. 3 is a graph comparing the results determined by this invention in Example 1 with the results by a usual method.

The glucoamylase preparation was assayed according to the method of this invention and a usual method. The results are shown in FIG. 3. The present method in the drawing means the determination method using G2-N as a substrate, and the usual method means the method of "Annotation of No. 4 Revised Assays Prescribed by National Tax Administration Agency" using soluble starch as a substrate. From this drawing, a high correlation is recognized between the present method and the usual method.

(9) Influence of glucose concentration

Figure 4:
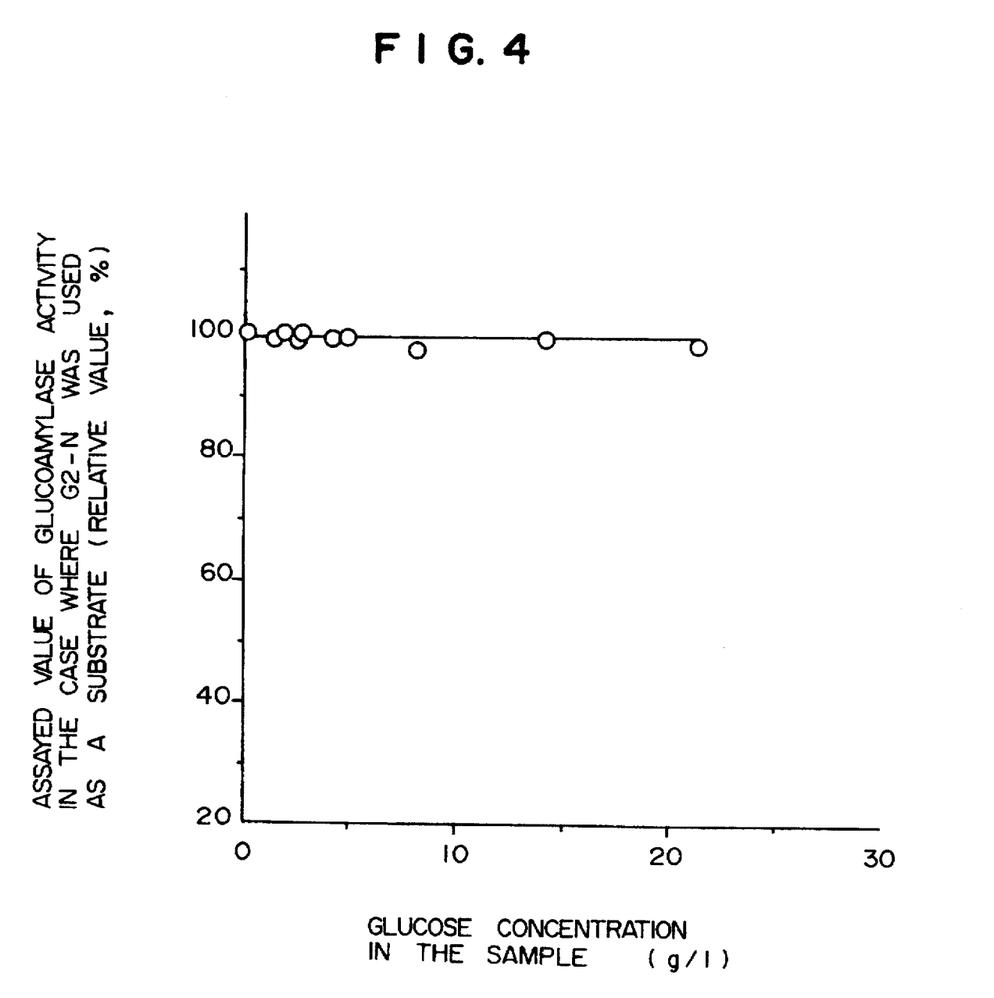
FIG. 4 is a graph showing the influence of the concentration of glucose on the reaction in Example 1.

Glucose was added to the glucoamylase preparation to make the glucose concentration 0 to 22 g/l, and the resultant solutions as enzyme samples were subjected to reaction. The results are shown in FIG. 4.

It is seen from this drawing that a measured value is not influenced by glucose up to the glucose concentration of at least 22 g/l.

(10) Determination of Km value

The Km value of the glucoamylase preparation on G2-N was measured, and found to be 0.0429 mM.

EXAMPLE 3

Preparation of reagents for determining an exo-type saccharide hydrolase activity (1) Preparation of a β-maltoside derivative substrate solution In the same manner as in (1) of Example 1, G2-N was dissolved so that its concentration could become 1 mM.

(2) Preparation of a coupled enzyme solution

Prepared in the same manner as in (2) of Example 1.

EXAMPLE 4

Determination of an α-glucosidase solution (1) Preparation of a β-maltoside derivative substrate solution As is the case with (1) of Example 1, G2-N was dissolved so that its concentration could become 1 mM.

(2) Preparation of a coupled enzyme solution

Prepared in the same manner as in (2) of Example 1.

(3) Preparation of a α-glucosidase preparation solution

Purified α-glucosidase obtained from a solid culture extract of *Aspergillus oryzae* using ion exchange chromatography was used after appropriate dilution with 100 mM acetate buffer (pH=5.0).

(4) Reaction procedures

① Reaction using G2-N as a substrate

Conducted in the same manner as in (4) of Example 2.

② Reaction using 4-nitrophenyl=α-D-glucoside (hereinafter, referred to as PNP-G) as a substrate.

The α-glucosidase activity was determined according to the assay method of "Methods in Enzymology, VIII", page 559, Academic Press (1966), using PNP-G as a substrate. As PNP-G was used one made by Nacalai Tesque Inc.

(5) Calculation of activity

① Activity in the case where G2-N was used as a substrate

Its activity on this substrate was determined in the same manner as in (5) of Example 2.

② Activity in the case where PNP-G was used as a substrate

As to the definition of its activity, an enzyme amount whereby 1 μmol of p-nitrophenol is liberated at 37° C. for 1 minute was defined as 1 U.

(6) Linearity of reaction

Figure 5:
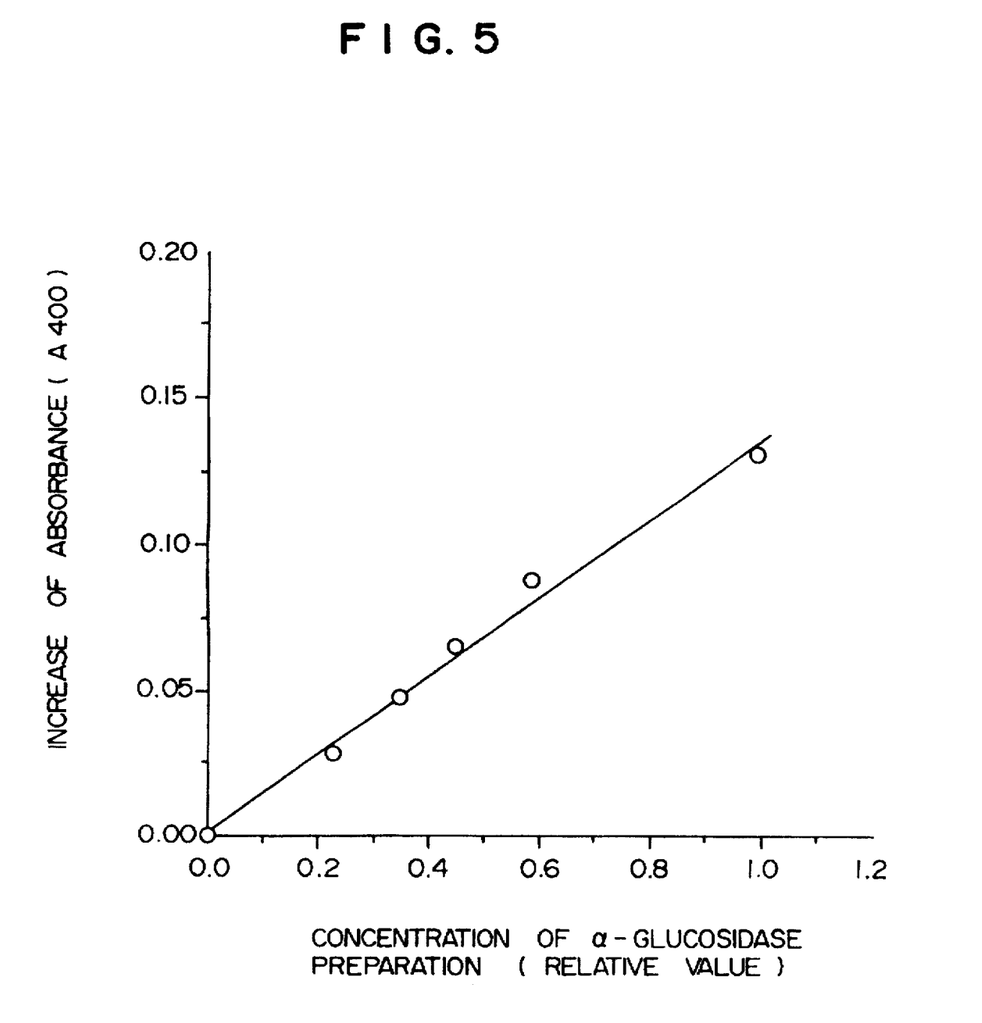
FIG. 5 is a graph showing the linearity of the reaction in Example 2.

Reaction was conducted using the α-glucosidase preparation and G2-N as a substrate, and absorbance was measured. The results are shown in FIG. 5. It is seen from this drawing that there is good linearity between the concentration of the α-glucosidase and the absorbance.

(7) Determination of α-glucosidase activity

Figure 6:
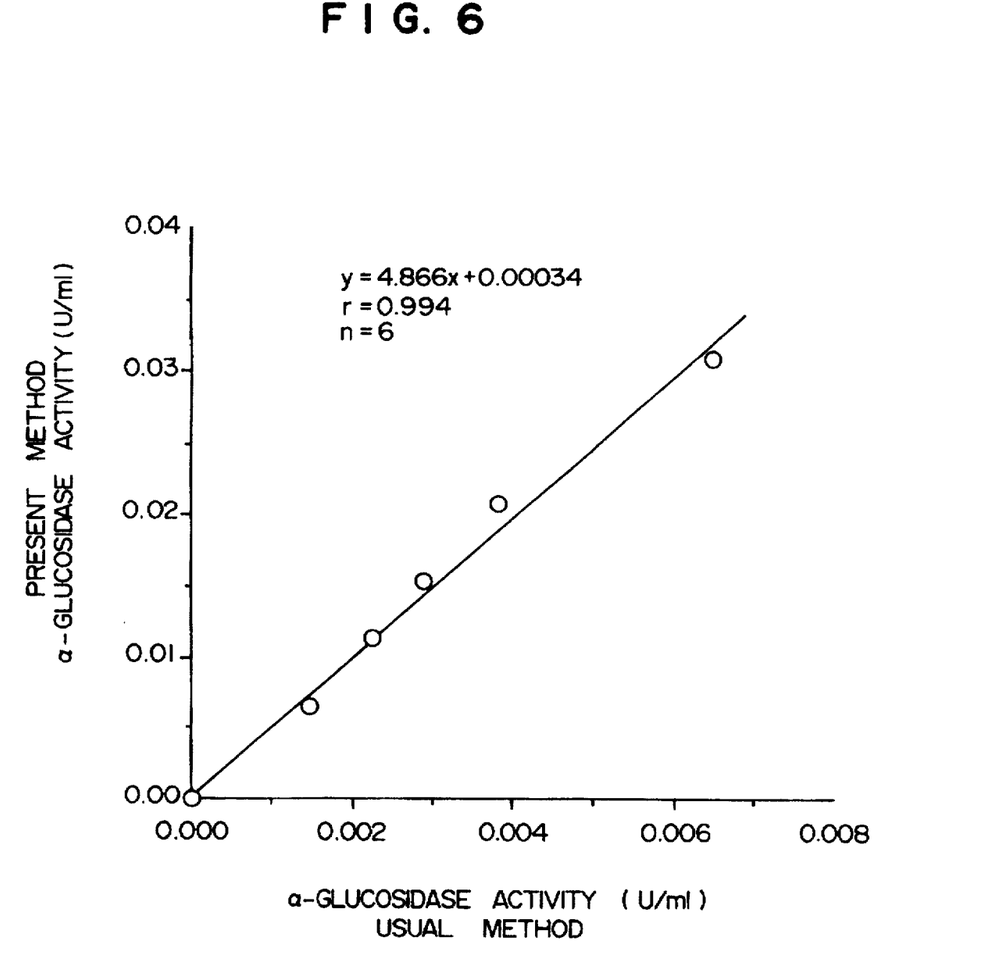
FIG. 6 is a graph for comparing the results determined by this invention in Example 2 with the results by a usual method.

The α-glucosidase preparation was assayed according to the method of this invention and a usual method. The results are shown in FIG. 6. The present method (method of this invention) in the drawing means the assay method using G2-N as a substrate, and the usual method means the method of "Methods in Enzymology, VIII", page 559, Academic Press (1966), using PNP-G as a substrate.

(8) Determination of Km value

The Km value of the α-glucosidase preparation on G2-N was measured, and found to be 0.0959 mM.

EXAMPLE 5

Determination of glucoamylase activity (1) Preparation of a substrate solution 4-nitrophenyl O -α-D-glucopyranosyl-β-D-glucopyranoside (hereafter, abbreviated as G2-PNP) was dissolved in 100 mM acetate buffer (pH=4.0) so that its concentration could become 10 mM.

(2) Preparation of a coupled enzyme solution

A coupled enzyme solution was prepared in the same manner as in (2) of Example 2.

(3) Preparation of a sample

The same glucoamylase preparation as in (3) of Example 2 was used. The sample was appropriately diluted using 100 mM acetate buffer (pH=5.0).

(4) Reaction procedures

Reaction was conducted in the same manner as in (4) of Example 2.

(5) Determination results

Figure 7:
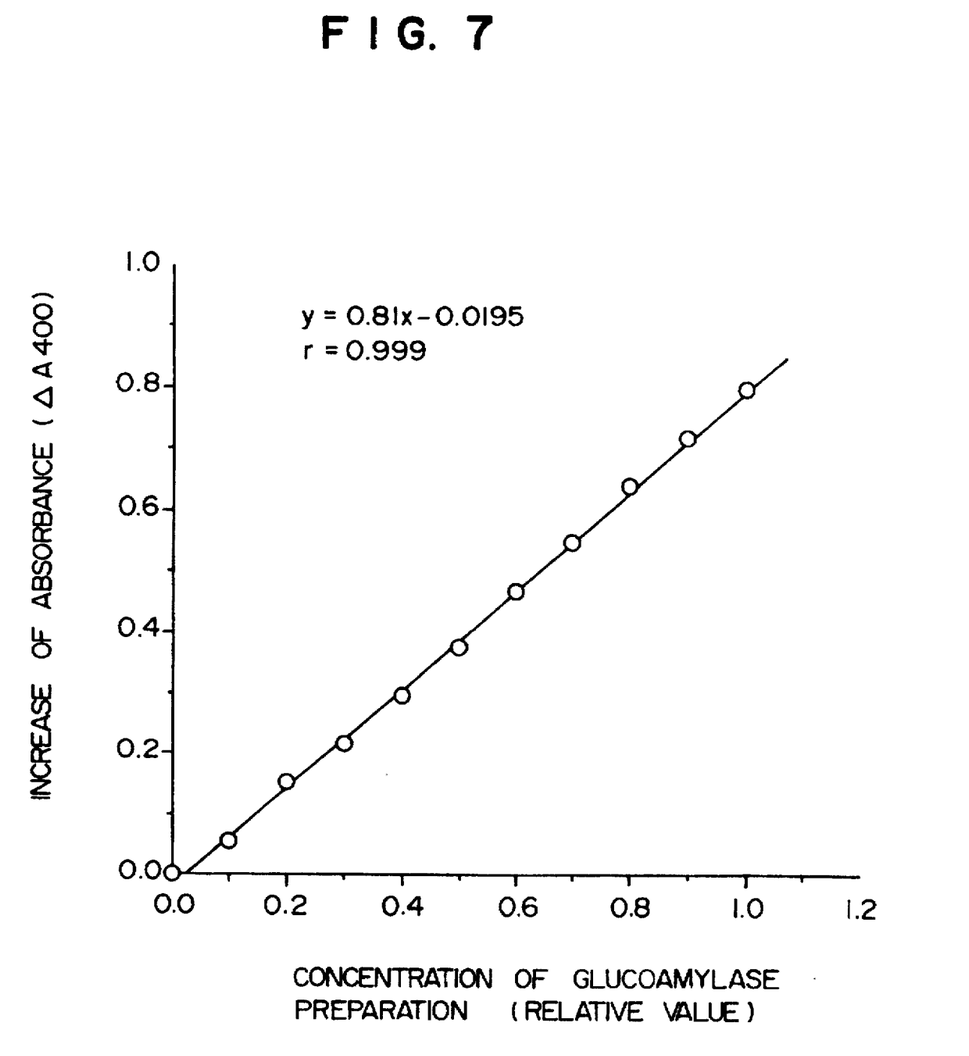
FIG. 7 is a graph showing the time course of the reaction in Example 3.

The results of determination are shown in FIG. 7. It is seen from the drawing that there is good linearity between the concentration of the glucoamylase and the increase of absorbance.

EXAMPLE 6

Determination of the exo-type saccharide hydrolase activity in an extract of rice Koji (1) Preparation of a substrate solution A substrate solution was prepared in the same manner as in (1) of Example 2. The substrate concentration was adjusted to 10 mM.

(2) Preparation of a coupled enzyme

A coupled enzyme was prepared in the same manner as in (2) of Example 2.

(3) Preparation of a sample 10 g each of 12 kinds of rice Koji were weighed out. To each of them was added 50 ml of 10 mM acetate buffer (pH=5.0) containing 0.5% by weight of NaCl was added, and the mixture was subjected to exudation at room temperature for 3 hours with occasional shaking, and then filtered. The resultant filtrate is referred to as the extract before dialysis. 10 ml of the filtrate was put in a dialysis membrane, dialyzed at 5° C. overnight against 10 mM acetate buffer (pH=5.0), and then diluted to 20 ml with water. This is referred to as the extract after dialysis.

(4) Reaction procedures

Reaction was conducted in the same manner as in (4) of Example 2.

(5) Calculation of activity

The activity of an enzyme sample was calculated in the same manner as in (5) of Example 2.

(6) Determination results

Figure 8:
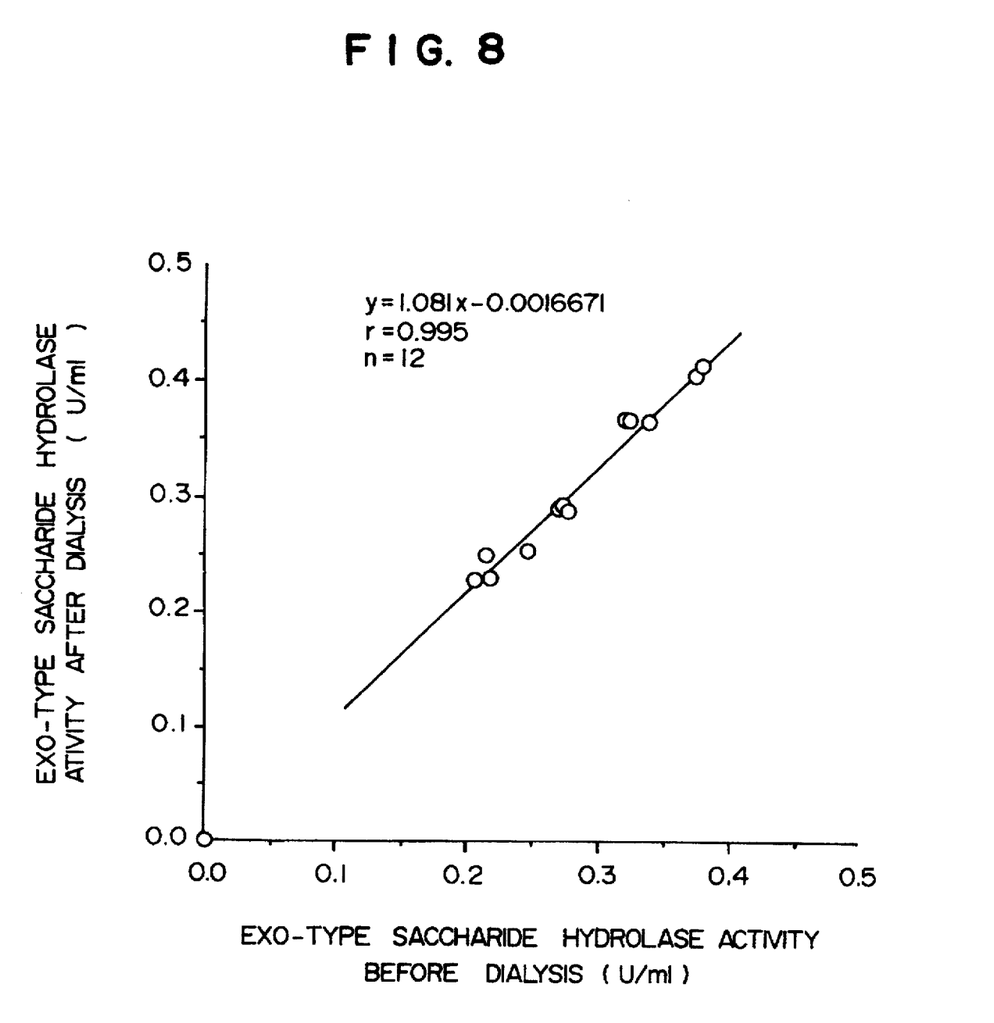
FIG. 8 is a graph showing the results determined on the sample before the dialysis and the sample after the dialysis of the extract of the rice Koji in Example 4.

Enzymatic activities were assayed using the rice Koji extracts before and after dialysis as enzyme samples. The results are shown in FIG. 8. It is seen from the drawing that it is possible, according to the method of this invention, to assay the exo-type saccharide hydrolase activity contained in a sample without conducting dialysis treatment.

EXAMPLE 7

Differential determination test

A glucoamylase preparation and an α-glucosidase preparation whose activities are known were mixed in various proportions and G2-N was used as the first substrate and PNP-G as the second substrate. On the above occasion, conformity was checked between theoretical values obtained based on the mixing ratios and calculated values calculated from Equation 3 and 4.

(1) Determination using G2-N

The preparation of a substrate solution and a coupled enzyme, and assay were conducted in the same manner as in Example 2, except that the amount of 0.2M $Na_2CO_3$ solution to be added at the time of the stop of reaction was made to be 1,000 µl. The activity of an enzyme sample was calculated as follows.

$$U/ml = \Delta A \times 0.237 \times df$$

(2) Determination using PNP-G

The preparation of a substrate solution and assay were conducted in the same manner as in Example 4.

(3) Determination results

① Calculation of reaction rate coefficients $$k_1 = 5.58(\Delta OD \cdot U/ml)$$

$$k_3 = 0(\Delta OD \cdot U/ml)$$

were obtained from the increases of absorbance and the enzymatic activities obtained when the glucoamylase preparation, and G2-N and PNP-G as substrates were used. Herein, as the glucoamylase activity value was used one obtained when G2-N was used as a substrate.

The increases of absorbance and the enzymatic activities were measured using the α-glucosidase preparation and G2-N and PNP-G as substrates, and as a result, $$k_2 = 104.8(\Delta OD \cdot U/ml)$$

$$k_4 = 33.9(\Delta OD \cdot U/ml)$$

were obtained. Herein, as the α-glucosidase activity value was used one obtained when PNP-G was used as a substrate.

② Glucoamylase activity

Figure 9:
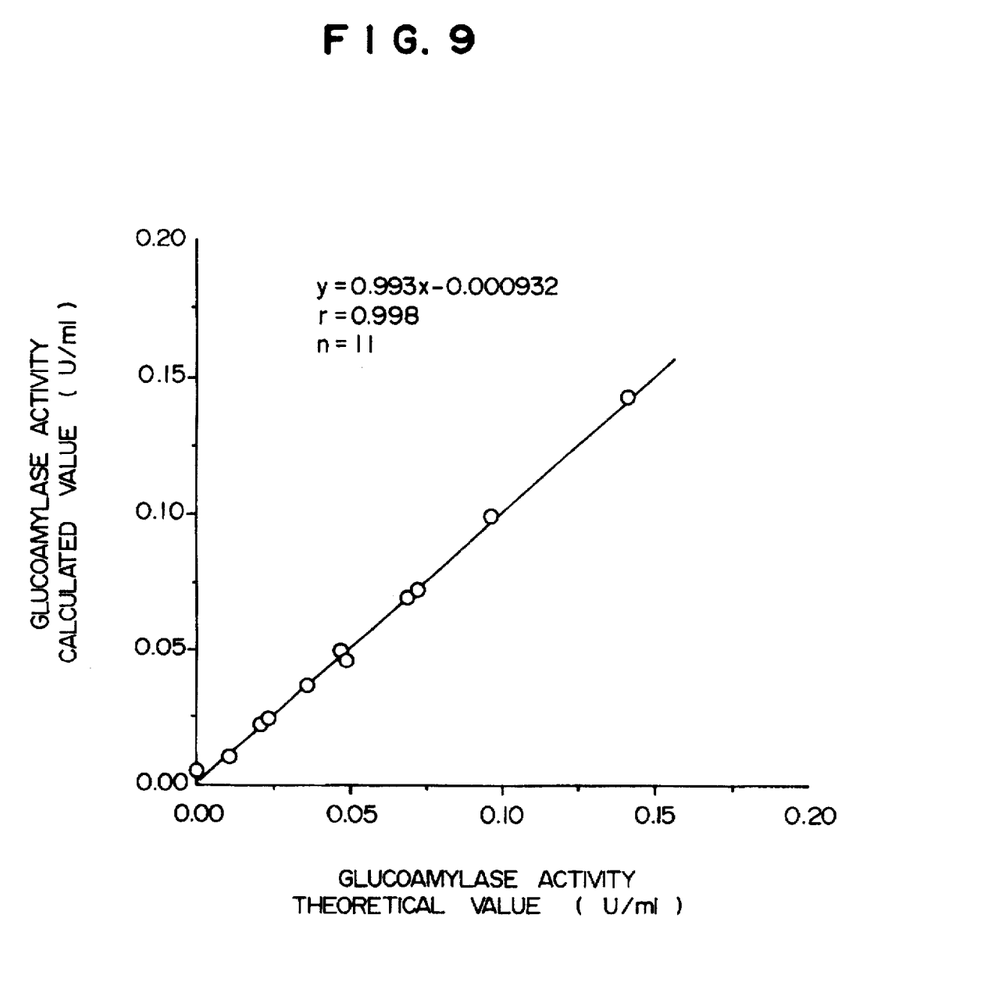
FIG. 9 is a graph showing the relation between the theoretical value and the calculated value of glucoamylase activity in Example 5.

A value calculated from glucoamylase activity before the mixing was assumed to be a theoretical activity value, and a value calculated by entering the reaction rate coefficient in (Equation 3) was assumed to be a calculated activity value. The relation between these values is shown in FIG. 9. It is seen from the drawing that the theoretical activity value and the calculated activity value accord adequately.

③ α-glucosidase activity

When PNP-G was used as a substrate, the glucoamylase did not act thereon at all ($k_3=0$). Namely, the result obtained when assay was conducted using PNP-G as a substrate gives an α-glucosidase activity.

EXAMPLE 8

Differential determination test

The glucoamylase preparation and the α-glucosidase preparation were appropriately diluted, and G2-N was used as the first substrate and 2-chloro-4-nitrophenyl=α-D-glucopyranoside (hereafter, abbreviated as N-G) as the second substrate. On the above occasions, their respective reaction rate coefficients were checked.

(1) Determination using G2-N

In the same manner as in Example 2, a substrate solution and a coupled enzyme were prepared, and measurement was conducted.

(2) Determination using N-G

① Preparation of a substrate solution

N-G was dissolved in 100 mM acetate buffer (pH=4) so that its concentration could become 10 mM.

② Reaction procedures

500 µl of the substrate solution was preliminarily warmed at 37° C. for 5 minutes. 25 µl of the α-glucosidase preparation solution or the glucoamylase preparation solution was added to start reaction. After the reaction at 37° C. for accurately 10 minutes, 500 µl of 0.2M $Na_2CO_3$ solution was added to stop the reaction. The absorbance of this solution at 400 nm was measured. As to blank, the mixed solution of the substrate and the coupled enzyme was left alone at 37° C. for 10 minutes, 500 µl of 0.2M $Na_2CO_3$ solution was added and mixed, and then the glucoamylase preparation solution or the α-glucosidase preparation solution was added. Thereafter, absorbance was measured in the same manner as above.

(3) Calculation of activity

The activity of the enzyme sample on this substrate was calculated as follows from the obtained absorbance.

$$U/ml = \frac{\Delta A \times Vt \times df}{\epsilon \times Vs \times t}$$

$$= \Delta A \times 0.237 \times df$$

wherein U is an enzyme amount whereby 1 µl mol of 2-chloro-4-nitrophenol is liberated at 37° C. for 1 minute, $\Delta A$ is a value obtained by subtracting the absorbance of blank from the absorbance of the enzyme sample, Vt is the amount of the reaction solution, df is the dilution rate of the sample, $\epsilon$ is the molecular extinction coefficient of 2-chloro-4-nitrophenol (17.3 $cm^2$/µmol), Vs is the liquid amount of the enzyme sample, and t is reaction time (minute).

(4) Determination results $$k_1 = 4.22(\Delta OD \cdot U/ml)$$

$$k_3 = 0.514(\Delta OD \cdot U/ml)$$

were obtained from the increases of absorbance and the enzymatic activities obtained when the glucoamylase preparation, and G2-N and N-G as substrates were used. Herein, as the glucoamylase activity value was used one obtained when G2-N was used as a substrate.

The increases of absorbance and the enzymatic activities were measured using the α-glucosidase preparation and G2-N and N-G as substrates, and as a result, $$k_2 = 20.51(\Delta OD \cdot U/ml)$$

$$k_4 = 119.49(\Delta OD \cdot U/ml)$$

were obtained. Herein, as the α-glucosidase activity value was used one obtained when PNP-G was used as a substrate.

Informative Examples are shown below.

Informative Example 1 Production of G2-N 10.0 g (27.8 mmol) of commercially available maltose monohydrate (made by Wako Pure Chemical Industries, Ltd.) was dissolved in 200 ml of pyridine, 100 ml (1.06 mol) of acetic anhydride was added, reaction was conducted at room temperature for 2 days, and pyridine, acetic anhydride and acetic acid in the reaction solution were distilled out. The residue was dissolved, without being purified by chromatography or the like, in 100 ml of dichloromethane, 2.64 ml (27.8 mmol) of phosphorus tribromide and 1.00 ml (55.5 mmol) of water were added, and reaction was conducted at room temperature for 10 hours under stirring. Then, 26.9 g of (195 mmol) of anhydrous potassium carbonate was added to the reaction solution, and reaction was conducted at room temperature for 15 minutes under stirring. The insoluble matter was filtered with a glass filter, and washed three times with 300 ml portions of dichloromethane. The filtrate and the washings were combined, and dichloromethane contained therein was distilled out. The resultant residue was dissolved, without being purified by chromatography, or the like, in 100 ml of acetonitrile, 14.5 g (83.6 mmol) of 2-chloro-4-nitrophenol was added, further, 19.4 g (83.6 mmol) of silver oxide ($Ag_2O$) was added, and reaction was conducted at 35° C. for 17 hours under stirring. The reaction solution was then filtered with a glass filter, and the filter cake was washed three times with 200 ml portions of dichloromethane. The filtrate and the washings were combined and concentrated under reduced pressure to distil out acetonitrile and dichloromethane contained therein. 1.0 liter of dichloromethane was added to the residue, and the mixture was cotton plug filtered. The filtrate was washed once with 500 ml of 0.5N aqueous sodium hydroxide solution and three times with 500 ml portions of saturated saline, dried with addition of 20 g of anhydrous sodium sulfate, cotton plug filtered, and then concentrated under reduce pressure to distil out dichloromethane contained therein. The residue was suspended, without being purified, in a mixed liquid of 200 ml of methanol, 100 ml of 28% by weight of ammonia water and 50 ml of water, and reaction was conducted at 35° C. for 20 hours under stirring. Then, the reaction solution was concentrated under reduced pressure to distil out water and methanol contained therein. The resultant residue was purified by ODS gel column chromatography, the desired fractions eluted with acetonitrile-water mixture (volume ratio 1:4) were concentrated, and the concentrate was recrystallized from water to give 5.81 g (11.7 mmol, 4 steps overall yield 42%) of the desired G2-N.

Melting point (° C.): 185–187

Ultraviolet region and visible region absorption spectrum:

Absorption maximum wavelength [maximal value in methanol] (nm)=289 (log $\epsilon$=3.92), 227 (log $\epsilon$=3.92), 2.09 (log $\epsilon$=4.11)

Infrared absorption spectrum ($cm^{-1}$): 3363, 2932, 1587, 1510, 1488, 1349, 1274, 1082, 1042

Nuclear magnetic resonance spectrum (200 MHz) ppm (DNSO-$d_6$/$D_2O$=10:1, v/v): 3.05–3.80 (m), 5.11 (1H, d, J=3.7 Hz), 5.26 (1H, d, J=7.6 Hz), 7.48 (1H, d, J=9.3 Hz), 8.19 (1H, dd, J=9.3 Hz, 2.7 Hz), 8.31 (1H, d, J=2.7 Hz)

High performance liquid chromatography [made by TOSOH CORPORATION, TSKgel Amide-80 column (4.6 mmID×250 mm), RI detection, eluent:acetonitrile/water =85:15 (v/v), flow rate: 1.0 ml/min: $t_R$=8.6 min Specific rotation ($[\alpha]_D^{25}$): (c 0.500, $H_2O$: +4.5°

Elementary analysis for $C_{18}H_{24}ClNO_{13}$:

|  | C | H | N |
|---|---|---|---|
| Calculated (%): | 43.43 | 4.86 | 2.81 |
| Found (%): | 43.29 | 4.95 | 2.68 |

Informative Example 2 Production of G2-PNP

The same operations as in Informative Example 1 were conducted except that 11.6 g (83.6 mmol) of 4-nitrophenol was used in place of 2-chloro-4-nitrophenol, the resultant residue was purified by ODS gel column chromatography, and the desired fractions eluted with an acetonitrile-water mixture (volume ratio 15:85) were concentrated, and recrystallized from water to give 4.91 g (10.6 mmol, 4 steps overall yield 38%) of the desired G2-PNP.

Melting point (° C): 133–135 (decomposed)

Ultraviolet region and visible region absorption spectrum:

Absorption maximum wavelength [maximal value in methanol] (nm)=295 (log $\epsilon$=4.23), 219 (log $\epsilon$=4.06), 203 (log $\epsilon$=4.12)

Infrared absorption spectrum ($cm^{-1}$): 3394, 2927, 1610, 1593, 1509, 1497, 1347, 1251, 1147, 1073, 1051

Nuclear magnetic resonance spectrum (200 MHz) ppm (DMSO-$d_6$/$D_2O$=10:1, v/v): 3.05–3.80 (m), 5.08 (1H, d, J=3.7 Hz), 5.14 (1H, d, J=7.8 Hz), 7.24 (2H, d, J=9.3 Hz), 8.20 (2H, d, J=9.3 Hz)

High performance liquid chromatography [made by TOSOH CORPORATION, TSKgel Amide-80 column (4.6 mmID×250 mm), RI detection, eluent:acetonitrile/water =75:25 (v/v), flow rate: 1.0 ml/min: $t_R$=4.9 min Specific rotation ($[\alpha]_D^{25}$): (c 0.500, $H_2O$): +3.1°

Elementary analysis for $C_{18}H_{25}NO_{13}$:

|  | C | H | N |
|---|---|---|---|
| Calculated (%): | 46.66 | 5.44 | 3.02 |
| Found (%): | 46.45 | 5.27 | 2.88 |

Informative Example 3 Production of N-G 20.0 g (51.3 mmol) of commercially available pentaacetyl-$\beta$-D-glucose [manufactured by Tokyo Kasei Co., Ltd.] was dissolved in a mixture of 28 ml of pyridine and 2.0 ml of acetic anhydride, 89 g (513 mmol) of 2-chloro-4-nitrophenol and 7.0 g (51.4 mmol) of zinc chloride ($ZnCl_2$) were added, reaction was conducted at 110° C. for 30 minutes under reduced pressure (20 mmHg) and stirring, and 50 ml of DMSO and 1.0 liter of dichloromethane were added under stirring. The mixture was washed three times with 1.0 liter portions of 0.1N NaOH aqueous solution and three times with 1.0 liter portions of 3% by weight aqueous NaCl solution, dried with addition of anhydrous sodium sulfate, cotton plug filtered, and concentrated under reduced pressure to distil out dichloromethane contained therein. The residue was suspended, without being purified by column chromatography or the like, in 930 ml of a mixture of concentrated hydrochloric acid-methanol-chloroform (1:10:4, v/v/v), and reaction was conducted at 25° C. for 2 days under stirring. 2N NaOH was added to the reaction solution to make the pH 5.5, and the mixture was concentrated under reduced pressure to distil out methanol and chloroform. 1.0 liter of water was added to the concentrate, the mixture was washed three times with 0.5 liter of dichloromethane, and then dichloromethane contained in a trace amount was distilled out. 3,000 U of β-glucosidase was added thereto, and reaction was conducted at 40° C. for 2 days under stirring. Concentrated hydrochloric acid was added to the enzymatic reaction solution to make the pH 3.0, reaction was conducted at 80° C. for 1 hour under stirring. 2N NaOH aqueous solution was added to make the pH 6.0, and the mixture was filtered with a Celite bed. The resultant filtrate was purified by ODS gel column chromatography, and the desired fractions eluted with an acetonitrile-water mixture (volume ratio 1:4) were concentrated, and recrystallized from water to give 3.76 g (11.2 mmol, 2 steps overall yield 22%) of the desired N-G.

Melting point (° C.): 160–162

Ultraviolet region and visible region absorption spectrum:

Absorption maximum wavelength [maximal value in methanol] (nm)=291 (log ε=3.91), 227 (log ε=3.91), 209 (log ε=4.08)

Infrared absorption spectrum (cm$^{-1}$): 3394, 2954, 1585, 1517, 1488, 1351, 1270, 1133, 1096, 1054

Nuclear magnetic resonance spectrum (200 MHz) ppm (CD$_3$OD): 3.05–4.15 (m), 4.43 (1H, d, J=7.6 Hz), 5.73 (1H, d, J=3.7 Hz), 7.42 (1H, d, J=9.3 Hz), 8.10 (1H, d, J=2.7 Hz)

High performance liquid chromatography [made by TOSOH CORPORATION, TSKgel Amide-80 column (4.6 mmID×250 mm), RI detection, eluent:acetonitrile/water =10:1 (v/v), flow rate: 1.0 ml/min: t$_R$=9.7 min Specific rotation ([α]$_D$ $^{25}$): (c 0.500, H$_2$O): +134°

| Elementary analysis for C$_{12}$H$_{14}$ClNO$_8$: | | | |
|---|---|---|---|
| | C | H | N |
| Calculated (%): | 42.94 | 4.20 | 4.17 |
| Found (%): | 42.69 | 4.35 | 4.04 |

A Comparative Example is set forth below.
Comparative Example 1 Comparison with the method using phenyl α-D-glucoside (1) Preparation of a substrate solution Phenyl α-D-glucoside was dissolved in 100 mM acetate buffer (pH=5.0) so that its concentration could become 10 mM.

(2) Preparation of a sample 4 mg of glucoamylase made by TOYOBO CO., LTD. was dissolved in 100 mM acetate buffer (pH=5.0).

(3) Reaction procedures 3.5 ml of the enzyme sample was mixed with 3.5 ml of the substrate solution, the mixture was subjected to incubation at 37° C., sampling was conducted every definite time, and absorbance at 270 nm was measured.

(4) Determination procedures for the present method

Determination was conducted in the same manner as in Example 1. As to the sample therefor, the same one as in (2) was used.

(5) Determination results

Figure 10:
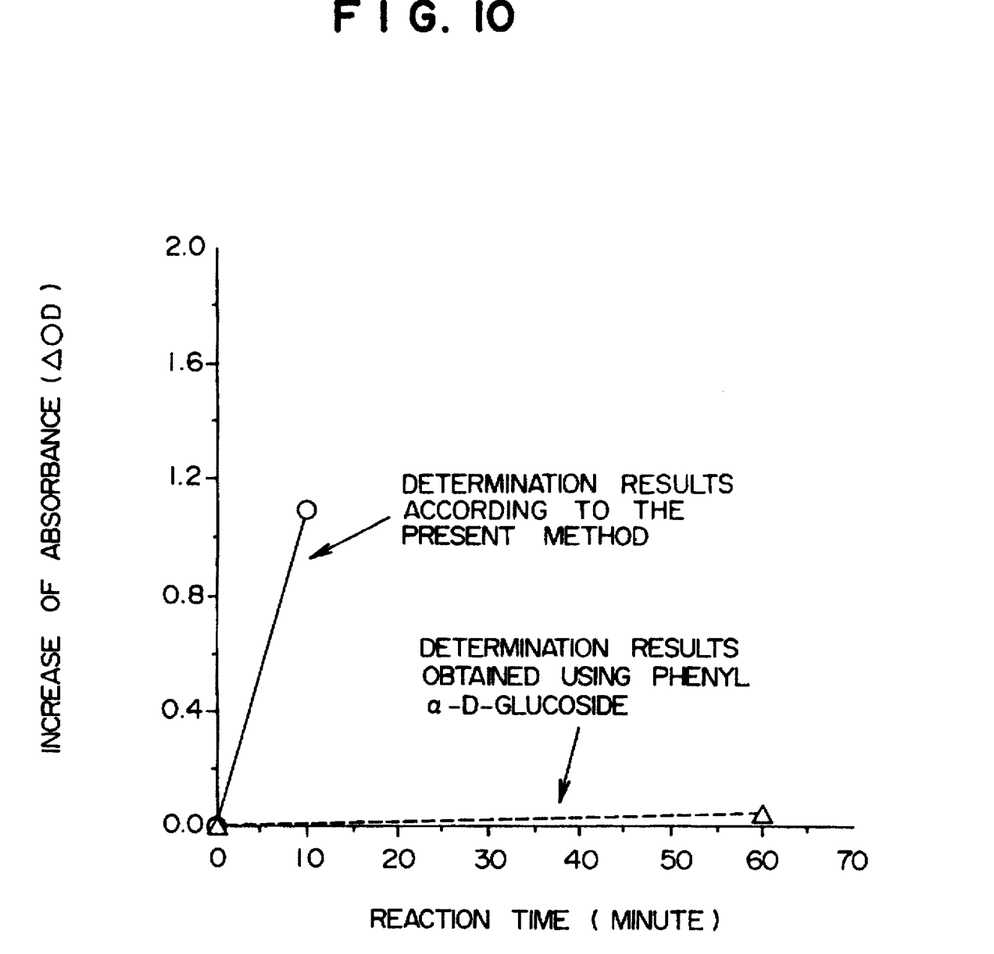
FIG. 10 is a graph comparing the increased absorbance as the result determined by this invention and the result by the comparative Example in Comparative Example 1.

Determination results are shown in FIG. 10. The results were compared by the increases of absorbance measured by the respective methods. It is seen therefrom that measurement is impossible in the case of phenyl α-D-glucoside.

What is claimed is:

1. A method for determining an exo-type saccharide hydrolase activity which comprises subjecting a sample containing the exo-type saccharide hydrolase to enzymatic reaction, using a β-maltoside derivative represented by the general formula:

wherein R is a chromophoric organic group, as a substrate, and β-glucosidase, and then quantitatively determine the chromophoric substance liberated using a spectral characteristic of said substance.

2. The method according to claim 1 wherein a β-maltoside derivative represented by the general formula wherein X$^1$ and X$^2$, which are same or different, are hydrogen atom, halogen atom, nitro group, amino group, alkyl group, sulfon group or carboxyl group, and is used as the substrate.

3. The method according to claim 1 or 2 wherein a β-maltoside derivative represented by the general formula wherein X$^1$ is a hydrogen atom, a halogen atom, a nitro group, an amino group, an alkyl group, a sulfon group or a carboxyl group, is used as the substrate.

4. A method for differentially determining glucoamylase and α-glucosidase activities which comprises subjecting a sample containing at least one of glucoamylase and α-glucosidase to separate enzymatic reactions, using, as the first substrate, a β-maltoside derivative represented by the general formula wherein R is a chromophoric organic group, in the presence of β-glucosidase, and using, as the second substrate, an α-glucoside derivative represented by the general formula wherein R' is a chromophoric organic group, and having such a property that the reaction rate ratio between glucoamylase and α-glucosidase is different from that on the first substrate, and then quantitatively determining the chromophoric substances liberated.

5. The method according to claim 4 wherein an α-glucoside derivative represented by the general formula wherein $X^3$ and $X^4$, which are same or different, are hydrogen atom, halogen atom, nitro group, amino group, alkyl group, sulfon group or carboxyl group, is used as the second substrate.

6. The method according to claim 4 or 5 wherein an α-glucoside derivative represented by the general formula wherein $X^3$ is a hydrogen atom, a halogen atom, a nitro group, an amino group, an alkyl group, a sulfon group or a carboxyl group, is used as the second substrate.

7. A reagent for determining an exo-type saccharide hydrolase activity, which comprises a β-maltoside derivative represented by the general formula wherein R is a chromophoric organic group, and β-glucosidase.

8. The method of claim 4 wherein the liberated chromophoric substances are determined using a spectral characteristic of said substances.

* * * * *